United States Patent [19]

Legrow et al.

[11] Patent Number: 5,157,139

[45] Date of Patent: Oct. 20, 1992

[54] INORGANIC ACID CATALYSED SILYLATION REACTIONS

[75] Inventors: Gary E. Legrow; Linda M. Madore; Milan F. Sojka; Richard B. Taylor; Norman E. Lake, all of Midland, Mich.

[73] Assignee: Dow Corning Corporation, Midland, Mich.

[21] Appl. No.: 770,376

[22] Filed: Oct. 3, 1991

[51] Int. Cl.$^5$ .............................................. C07F 7/18
[52] U.S. Cl. ................................................ 556/470
[58] Field of Search ..................................... 556/470

[56] References Cited

U.S. PATENT DOCUMENTS 3,529,006  9/1970  Senge ............................ 260/448.8
3,636,026  1/1972  Fuhr .............................. 250/448.8

OTHER PUBLICATIONS

Bazart et al.; "Organicsilicon Compounds", vol. 2, part 1, Academic Press, N.Y. (1965), p. 40.

*Primary Examiner*—Paul F. Shaver

[57] ABSTRACT

The present invention relates to a process for preparing clear and colorless alkoxysilane monomers from the reaction of a silazane with an organic alcohol in the presence of an inorganic acid catalyst. The inorganic acid catalyst is present in a critical range from 20 parts per million (ppm) to 300 ppm. Inorganic acid catalysts used within this critical range eliminate the need for a purification step in the process.

14 Claims, No Drawings

INORGANIC ACID CATALYSED SILYLATION REACTIONS

BACKGROUND OF THE INVENTION

The present invention relates to a process for preparing clear and colorless alkoxysilane monomers from the reaction of a silazane with an organic alcohol in the presence of an inorganic acid catalyst. The inorganic acid catalyst is present in a critical range from 20 parts per million (ppm) to 300 ppm. Inorganic acid catalysts used within this critical range eliminate the need for a purification step in the process.

Silylation is the introduction of a silyl group into a molecule in substitution for active hydrogen. It is known that organic compounds can be silylated by reaction with certain types of organosilicon compounds. For example, U.S. Pat. No. 3,636,026 discloses a silylation reaction in which hexamethyldisilazane is reacted with benzoin and sulfuric acid at 125° C., followed by a distillation to purify the crude product. It is important to note that the minimum amount of acid suggested in U.S. Pat. No. 3,636,026 is approximately 800 ppm. A silylation reaction is also disclosed in U.S. Pat. No. 3,529,006 in which N-methylolsilyl ethers are produced by reacting N-methylol compounds with an excess of hexamethyldisilazane in the presence of ammonium sulfate, a diluent is added and the product is filtered. In U.S. Pat. No. 3,529,006, the ammonium sulfate is formed in the silylation reaction using a minimum of 526 ppm of sulfuric acid.

The above mentioned processes have been employed successfully on a commercial scale for the preparation of pharmaceutical products. However, although the processes are capable of providing fairly good yields of the silylated product, the products formed by such processes must be purified by distillation and/or filtration before a clear and colorless product is obtained. The present inventors have discovered that haziness in the products of such processes is a result of the high levels of inorganic acids used in the silylation reactions. The level of inorganic acid employed determines the amount of the corresponding ammonium salt in the product. Such ammonium salts are insoluble and render the product hazy. A continuing need exists, therefore, for further improvements in silylation reactions to eliminate the purification process step while securing a transparent product.

The present inventors have discovered that the purification step in silylation reactions may be eliminated if between 20 ppm and 300 ppm of an inorganic acid catalyst is used. This was particularly unexpected since it was not known whether such small amounts of inorganic acid catalyst would take the reaction to completion. Moreover, inorganic acid catalysts employed within this critical range do not generate enough of the corresponding ammonium salts to render the product unclear. Thus, the alkoxysilane monomers formed from the process of the present invention are clear, colorless and odorless, and thus, may be formulated into a wide variety of products, such as cosmetics.

SUMMARY OF THE INVENTION

Accordingly, the present invention provides a process for preparing clear and colorless alkoxysilane monomers comprising: reacting at a temperature of from 40° C. to 125° C. in an inert, essentially anhydrous atmosphere (A) a silazane selected from the group consisting of a disilazane having the general formula

(R$_3$Si)$_2$NH, a cyclic silazane having the general formula

$$\left[ \begin{array}{c} R_2 \\ | \\ SiNH \end{array} \right]_x$$

and mixtures thereof,
wherein R is a monovalent hydrocarbon radical having from 1 to 8 inclusive carbon atoms and x is an integer from 3 to 6;

(B) an organic alcohol selected from the group consisting of a monohydric alcohol, a dihydric alcohol, a polyhydric alcohol and mixtures thereof; and (C) from 20 ppm to 300 ppm of an inorganic acid catalyst.

DETAILED DESCRIPTION OF THE INVENTION

Component (A) is a disilazane or a cyclic silazane. The disilazanes have the general formula

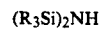

(R$_3$Si)$_2$NH wherein R is a monovalent hydrocarbon radical having from 1 to 8 inclusive carbon atoms. The cyclic silazanes have the general formula

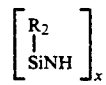

$$\left[ \begin{array}{c} R_2 \\ | \\ SiNH \end{array} \right]_x$$

wherein R is a monovalent hydrocarbon radical having from 1 to 8 inclusive carbon atoms, and x is an integer from 3 to 6. In the general formulae of the disilazane and cyclic silazane reactants employed in the process of this invention, each of the R substituents may be the same or different monovalent hydrocarbon radicals having from 1 to 8 carbon atoms. Examples of R substituents include alkyl radicals such as methyl, ethyl, butyl and 2,4,4-trimethylpentyl; alkenyl radicals such as vinyl and allyl; and aryl, alkaryl, aralkyl radicals such as phenyl, tolyl and benzyl. Preferably each of the R groups are methyl and x is 3. The silazanes useful in the present invention include:

1,3-bis(chloromethyl)tetramethyldisilazane,
di-n-octyltetramethyldisilazane, 1,3-diphenyltetramethyldisilazane,
1,3-divinyltetramethyldisilazane,
1,3-divinyl-1,3-diphenyl-1,3-dimethyldisilazane,
1,1,3,3,5,5,-hexamethylcyclotrisilazane, hexamethyldisilazane, octamethylcyclotetrasilazane, trimethyltrivinylcyclotrisilazane, and
1,1,3,3,-tetraphenyl-1,3-dimethyldisilazane. These silazanes are commercially available from Petrarch Systems, Incorporated, Bristol, PA.

Component (B) is an organic alcohol which is a monohydric alcohol, a dihydric alcohol or a polyhydric alcohol. Component (B) includes alcohols having from 1 to 24 carbon atoms, for example, aliphatic alcohols, such as methanol, ethanol, propanol, octadecanol, etc.; ether alcohols, such as methoxyethanol, ethoxyethanol, butoxyethanol, etc.; and glycerol. In addition, component (B) includes polyglycol ethers, such as methoxypolyethylene glycol. Component (B) may also be a mixture of organic alcohols. Preferred organic alcohols for the purposes of the present invention are stearyl alcohol, $HO(CH_2CH_2O)_{20}CH_3$, $HO_3(CH_2CH_2O)_{16}CH_3$ and $HO(CH_2CH_2O)_{12}CH_3$.

Component (C) is an inorganic acid catalyst which promotes the silylation reaction of the present invention. Component (C) is present in a critical amount from 20 ppm to 300 ppm. A preferred amount of the inorganic acid catalyst, component (C), is from 20 to 160 ppm. A more preferred amount of component (C) is from 40 to 100 ppm. Inorganic acid catalysts used within this critical range generate clear, colorless products without the need for a purification step in the process. Inorganic acid catalysts used outside of this range produce products which contain a precipitate, appear hazy and/or have a yellowish tint. Thus, products formed using inorganic acid catalysts that fall outside the critical range must be purified by distillation and/or filtration before a clear and colorless product is obtained. It should be noted that inorganic acid catalysts used at the upper end of the critical range may result in products which are not as clear and colorless as products produced using inorganic acids in the preferred and more preferred ranges. In such instances, however, a purification step is not necessary since the products are only slightly colored and/or slightly hazy due to an insignificant amount of ammonium salt precipitate. Operable inorganic acid catalysts are, for example, phosphoric acid and sulfuric acid.

The process of the present invention is carried out by mixing the silazane compound, component (A), the alcohol, component (B), and the inorganic acid catalyst, component (C). Generally, the manner in which these components are mixed together is not important. The components are brought together in an inert, essentially anhydrous atmosphere. By inert it is meant that the reaction is carried out under a blanket of inert gas such as argon, nitrogen or helium. What is meant by essentially anhydrous is that the reaction is preferably carried out in an absolutely anhydrous atmosphere but minute amounts of moisture can be tolerated.

The desired temperature range for the reaction is 40° C. to 125° C. A preferred temperature range is 50° C. to 70° C. The components are stirred and allowed to react for between 10 to 90 minutes whereupon the temperature and agitation are maintained and the ammonia generated from the reaction is removed. The method of ammonia recovery is not critical and can be by any convenient means. Methods such as simple evaporation or stripping under heat and/or vacuum are known in the art and useful herein. The reaction is continued until evolution of ammonia has ceased. Applicants have determined that the length of time that the reaction requires depends on the temperature employed. Generally, the reaction time is between two and eighteen hours when the temperature is within the preferred range. Following removal of the ammonia, a base is added to neutralize the inorganic acid catalyst. Suitable bases include, for example, sodium bicarbonate and sodium hydroxide, etc.. The reaction product may optionally be filtered.

The product formed from the process of the present invention is an alkoxysilane monomer. Such alkoxysilanes may be employed in cosmetics, such as, in skin and hair conditioning products, moisturizers, lotions and cleansers; automotive care products, such as, in waxes, protectorants and polishes; and household products, such as, in cleaners, disinfectants and polishes.

The invention is further defined in the following examples wherein all parts and percentages are by weight and degrees are Celsius unless otherwise stated.

EXAMPLE I

A mixture of 572.1 grams of $HO(CH_2CH_2O)_{16}CH_3$, 0.095 grams of phosphoric acid (85% purity) and 23.25 grams of hexamethylcyclotrisilazane was prepared at 60° C. Agitation was applied to the mixture and after one hour the ammonia was removed by purging with nitrogen and vacuum pumping at 100 mm of Hg for 17 hours. Sodium bicarbonate, 0.205 grams, was added to the product to neutralize the phosphoric acid. The resulting product was clear and colorless. To determine if any ammonia remained in the product, 20.0 grams of product was diluted with 80.0 grams of water and the pH was measured. A pH reading of less than 7.0 was obtained, therefore, the silylation reaction was completed since no ammonia existed in the product.

EXAMPLE II

A mixture of 572.1 grams of a blend of $HO(CH_2CH_2O)_{20}CH_3$ and $HO(CH_2CH_2O)_{12}CH_3$, 0.095 grams of phosphoric acid (85% purity) and 23.25 grams of hexamethylcyclotrisilazane was prepared at 60° C. Agitation was applied to the mixture and after one hour the ammonia was removed by purging with nitrogen and vacuum pumping at 100 mm of Hg for 17 hours. Sodium bicarbonate, 0.205 grams, was added to the product to neutralize the phosphoric acid. The resulting product was clear and colorless. To determine if any ammonia remained in the product, 20.0 grams of product was diluted with 80.0 grams of water and the pH was measured. A pH reading of less than 7.0 was obtained, therefore, the silylation reaction was completed since no ammonia existed in the product.

EXAMPLE III

A mixture of 572.1 grams of $HO(CH_2CH_2O)_{16}CH_3$, 0.095 grams of sulfuric acid (97% purity) and 23.25 grams of hexamethylcyclotrisilazane was prepared at 60° C. Agitation was applied to the mixture and after one hour the ammonia was removed by purging with nitrogen and vacuum pumping at 100 mm of Hg for 15 hours. Sodium bicarbonate, 0.205 grams, was added to the product to neutralize the phosphoric acid. The resulting product was clear and colorless. To determine if any ammonia remained in the product, 20.0 grams of product was diluted with 80.0 grams of water and the pH was measured. A pH reading of less than 7.0 was obtained, therefore, the silylation reaction was completed since no ammonia existed in the product.

EXAMPLE IV

A mixture of 572.1 grams of $HO(CH_2CH_2O)_{16}CH_3$, 0.095 grams of phosphoric acid (99% purity) and 23.25 grams of hexamethylcyclotrisilazane was prepared at 60° C. Agitation was applied to the mixture and after one hour the ammonia was removed by purging with nitrogen and vacuum pumping at 100 mm of Hg for 17 hours. Sodium bicarbonate, 0.205 grams, was added to the product to neutralize the phosphoric acid. The resulting product was clear and colorless. To determine if any ammonia remained in the product, 20.0 grams of product was diluted with 80.0 grams of water and the pH was measured. A pH reading of less than 7.0 was obtained, therefore, the silylation reaction was completed since no ammonia existed in the product.

EXAMPLE V

A mixture of 572.1 grams of $HO(CH_2CH_2O)_{16}CH_3$, and 23.25 grams of hexamethylcyclotrisilazane was prepared at 60° C. Agitation was applied to the mixture and after one hour the ammonia was removed by purging with nitrogen and vacuum pumping at 100 mm of Hg for 48 hours. The resulting product was hazy and contained a high level of ammonia which was determined through pH measurement in which 20.0 grams of product was diluted with 80.0 grams of water and the pH was measured. A pH reading of greater than 7.0 was obtained, therefore, the silylation reaction was not completed since ammonia remained in the product.

EXAMPLE VI

A mixture of 211.25 grams of stearyl alcohol, 0.035 grams of phosphoric acid (99% purity) and 38.75 grams of hexamethyldisilazane was prepared at 65° C. After one hour, the ammonia was removed by purging with nitrogen and vacuum pumping at 100 mm of Hg for 12 hours at 65° C. The resulting product was clear and colorless. To determine if any ammonia remained in the product, 20.0 grams of product was diluted with 80.0 grams of isopropanol and the pH was measured. A pH reading of less than 7.0 was obtained, therefore, the silylation reaction was completed since no ammonia existed in the product.

EXAMPLE VII

A mixture of 84.5 grams of stearyl alcohol and 15.5 grams of hexamethyldisilazane was prepared at 75° C. The temperature was increased to 90° C. After eight hours, the ammonia was removed by purging with nitrogen and vacuum pumping at 100 mm of Hg for 8 hours. The resulting product was hazy and contained a high level of ammonia which was determined through pH measurement in which 20.0 grams of product was diluted with 80.0 grams of isopropanol and the pH was measured. A pH reading of greater than 7.0 was obtained, therefore, the silylation reaction was not completed since ammonia remained in the product.

EXAMPLE VIII

A mixture of 633.75 grams of stearyl alcohol, 0.225 grams of phosphoric acid (99% purity) and 116.25 grams of hexamethyldisilazane was prepared at 65° C. Agitation was applied to the mixture and during the first hour of reaction an exotherm of 4° C. was noticed. After one hour, the ammonia was removed by purging with nitrogen and vacuum pumping at 100 mm of Hg for 3 hours. Sodium bicarbonate, 0.563 grams, was added to the product to neutralize the phosphoric acid. The resulting product was slightly hazy. To determine if any ammonia remained in the product, 20.0 grams of product was diluted with 80.0 grams of isopropanol and the pH was measured. A pH reading of less than 7.0 was obtained, therefore, the silylation reaction was completed since no ammonia existed in the product.

It will be apparent from the foregoing that many other variations and modifications may be made in the structures, compounds, compositions and methods described herein without departing substantially from the essential features and concepts of the present invention. Accordingly, it should be clearly understood that the forms of the invention described herein are exemplary only and are not intended as limitations on the scope of the present invention.

What is claimed is:

1. A process for preparing clear and colorless alkoxysilane monomers comprising:
   reacting at a temperature of from 40° C. to 125° C. in an inert, essentially anhydrous atmosphere
   (A) a silazane selected from the group consisting of a disilazane having the general formula $(R_3Si)_2NH$, a cyclic silazane having the general formula

and mixtures thereof,
   wherein R is a monovalent hydrocarbon radical having from 1 to 8 inclusive carbon atoms and x is an integer from 3 to 6;
   (B) an organic alcohol selected from the group consisting of a monohydric alcohol, a dihydric alcohol, a polyhydric alcohol and mixtures thereof; and
   (C) from 20 ppm to 300 ppm of an inorganic acid catalyst.

2. The process of claim 1 wherein component (A) is hexamethyldisilazane.

3. The process of claim 1 wherein component (A) is 1,1,3,3,5,5,-hexamethylcyclotrisilazane.

4. The process of claim 1 wherein component (B) is an aliphatic alcohol.

5. The process of claim 4 wherein component (B) is stearyl alcohol.

6. The process of claim 1 wherein component (B) is an ether alcohol.

7. The process of claim 1 wherein component (B) is a polyglycol ether.

8. The process of claim 7 wherein component (B) is methoxypolyethylene glycol.

9. The process of claim 8 wherein component (B) is $HO(CH_2CH_2O)_{16}CH_3$.

10. The process of claim 8 wherein component (B) is a blend of $HO(CH_2CH_2O)_{20}CH_3$ and $HO(CH_2CH_2O)_{12}CH_3$.

11. The process of claim 1 wherein component (B) is present in an amount of from 20 ppm to 160 ppm.

12. The process of claim 11 wherein component (B) is present in an amount of from 40 ppm to 100 ppm.

13. The process of claim 1 wherein component (C) is sulfuric acid.

14. The process of claim 1 wherein component (C) is phosphoric acid.

* * * * *